United States Patent [19]

Storen

[11] Patent Number: 4,507,129

[45] Date of Patent: Mar. 26, 1985

[54] METHOD OF CLEANING DUST-CONTAINING GAS MIXTURES FROM A UREA PLANT

[75] Inventor: Harald Storen, Porsgrunn, Norway

[73] Assignee: Norsk Hydro a.s., Oslo, Norway

[21] Appl. No.: 452,045

[22] Filed: Dec. 22, 1982

[30] Foreign Application Priority Data

Jan. 7, 1982 [NO] Norway .................................. 820030

[51] Int. Cl.³ ............................................. B01D 47/06
[52] U.S. Cl. .......................................... 55/70; 55/84; 564/73
[58] Field of Search ................. 55/19, 70, 84; 564/68, 564/70, 72, 73; 71/28, 64.06

[56] References Cited

U.S. PATENT DOCUMENTS

| 2,977,386 | 3/1961 | Kise | 55/84 |
| 3,951,638 | 4/1976 | Bradley | 71/28 |
| 4,104,041 | 8/1978 | Arita et al. | 55/90 |
| 4,217,114 | 8/1980 | Lagana' et al. | 55/70 |

FOREIGN PATENT DOCUMENTS

| 802457 | 7/1949 | Fed. Rep. of Germany . | |
| 1128849 | 5/1962 | Fed. Rep. of Germany . | |
| 2513925 | 10/1980 | Fed. Rep. of Germany . | |
| 78974 | 7/1978 | Japan | 55/84 |
| 1572118 | 7/1980 | United Kingdom . | |
| 504546 | 5/1976 | U.S.S.R. | 55/84 |

Primary Examiner—David L. Lacey
Attorney, Agent, or Firm—Wenderoth, Lind & Ponack

[57] ABSTRACT

Gas mixtures from a urea plant, particularly such mixtures containing dust and especially off-gases from prilling towers or granulation units are cleaned. In order to prevent precipitation and accretion in the cleaning unit, there is applied an aqueous washing solution to which formaldehyde is added before it is brought in contact with the gas mixture. Formaldehyde is preferably added in the form of formaline, and the addition of formaline is regulated by pH-measurements in the washing solution such that pH is maintained at pH=6-8.5. The pH of the washing solution is preferably kept at pH=about 7, especially in order to obtain optimal removal of ammonia. The method is carried out during application of standard scrubbers in which aqueous washing solutions can be used.

4 Claims, 2 Drawing Figures

METHOD OF CLEANING DUST-CONTAINING GAS MIXTURES FROM A UREA PLANT

BACKGROUND OF THE INVENTION

The present invention relates to a method of cleaning gas mixtures from a urea plant, particularly such mixtures containing dust, and especially off-gases from prilling towers or granulation units and where the gases are scrubbed by an aqueous solution.

Urea prills or granules are produced from highly concentrated urea solutions or melts and treated in a prilling tower or granulation unit where air is used for cooling the product. The air drawn from these units must be cleaned before it is released into the atmosphere because it will contain urea dust, ammonia and different other decomposition products of urea.

The air drawn from the urea plant is scrubbed by an aqueous solution in order to reduce air pollution from the plant. This aqueous solution usually circulates in the scrubber until it has the desired concentration of urea, whereupon it is returned to the process for reclaiming urea. There are known several types of such scrubbers.

From DE-application No. 2,513,925 it is known to employ a venturi scrubber, in which water is mixed with the off-gases before they are conducted into the venturi scrubber. Water is primarily mixed with the off-gases in order to reduce plugging of the venturi nozzles by urea dust.

During washing of the off-gases from a prilling tower with a circulating aqueous urea solution, problems have been experienced with precipitation giving accretion and plugging of the scrubber. The precipitation resulted in increasingly thick accretions in the scrubber. Finally, dispersed mud sedimented in the tanks and pipes and a hard brittle coating occurred on all surfaces that came into contact with the washing solution. The nozzles for spraying liquid into the multiventuri were plugged and the ability of the unit to separate dust from water was soon strongly reduced.

The precipitates and the accretions were insoluble in water, and even when the supply of water was increased this did not help. Mechanical cleaning of the unit by scraping or the like of the deposits was accordingly very laborious and expensive.

SUMMARY OF THE INVENTION

The main object of the present invention is to provide a new method for washing off-gases from a urea plant so that precipitation of solid particles and formation of accretions in the scrubber can be avoided.

Another object is to provide a method to dissolve a deposit which already has been formed. It also is an object to improve removal of undesired gases in the off-gases and especially ammonia.

The effort of solving the problem was first started by studying the composition of the off-gases and then to determine the chemical and physical nature of the precipitates and the deposit. It is known that over a urea melt there will be a vapour pressure of decomposition products from urea, for instance ammonia and cyanic acid. When the melt is sprayed into a prilling tower or a granulation unit, there will be evaporation of decomposition products. Solid and urea droplets together with decomposition products of urea will partly be dissolved in the washing solution when brought into contact with the off-gases. A reaction between the different components in the solution is then evidently taking place, and a precipitate is formed which does not dissolve in water. To determine the reaction product proved to be difficult, but such product seemed to be a compound of cyanic acid, most likely a polymer. Therefore, an attempt was made to find a component which could neutralize the polymerization of cyanic acids. Both the absolute and relative amounts of the different components in the off-gases can vary, and this complicates the determination of possible reactions which might occur in the solution. A series of different reaction paths and products can be expected when all these components are present.

Experiments then were started in order to find suitable additives. When choosing additives one had to consider whether they could contaminate or in other ways damage the urea product.

As stated above, one wanted to reclaim the urea absorbed in the washing solution, and this is preferably carried out by continuously purging some of the urea solution circulating in the cleaning unit to the urea plant. Compounds added to the washing solution will accordingly end up in the urea product.

Having considered and tested several additives and thereupon rejected them because of negative results both in view of dissolving properties and contamination of the urea product, the inventors were finally left with formaldehyde as a possible additive to the washing solution. Formaldehyde was already used as an additive during the urea production, for increasing the crushing strength of the urea. It was then found that precipitation in the washing solution stopped and it was surprisingly found that formerly formed precipitate dissolved. After some time even the hard deposits started to dissolve, and the whole cleaning unit was cleaned in this way. The washing solution became completely clear, contrary to what it had been earlier when it was faded or contained milky precipitated compounds suspended in the solution.

The special feature of the method according to the invention is that during cleaning the gas mixture formaldehyde is added to the washing solution before it is brought in contact with the gas mixture.

The formaldehyde is preferably added to the washing solution as formaline, and the supply is regulated by means of pH-measurements in the washing solution, and the pH should be kept at pH=6-8.5.

The most preferred method is to continuously supply a controlled amount of formaline to the washing solution such that the pH=about 7.

BRIEF DESCRIPTION OF THE DRAWINGS

The applied apparatus which was a technical unit is shown in the attached drawings, and the invention will be further explained during the following description thereof and of the examples.

DETAILED DESCRIPTION OF THE INVENTION

Figure 1:
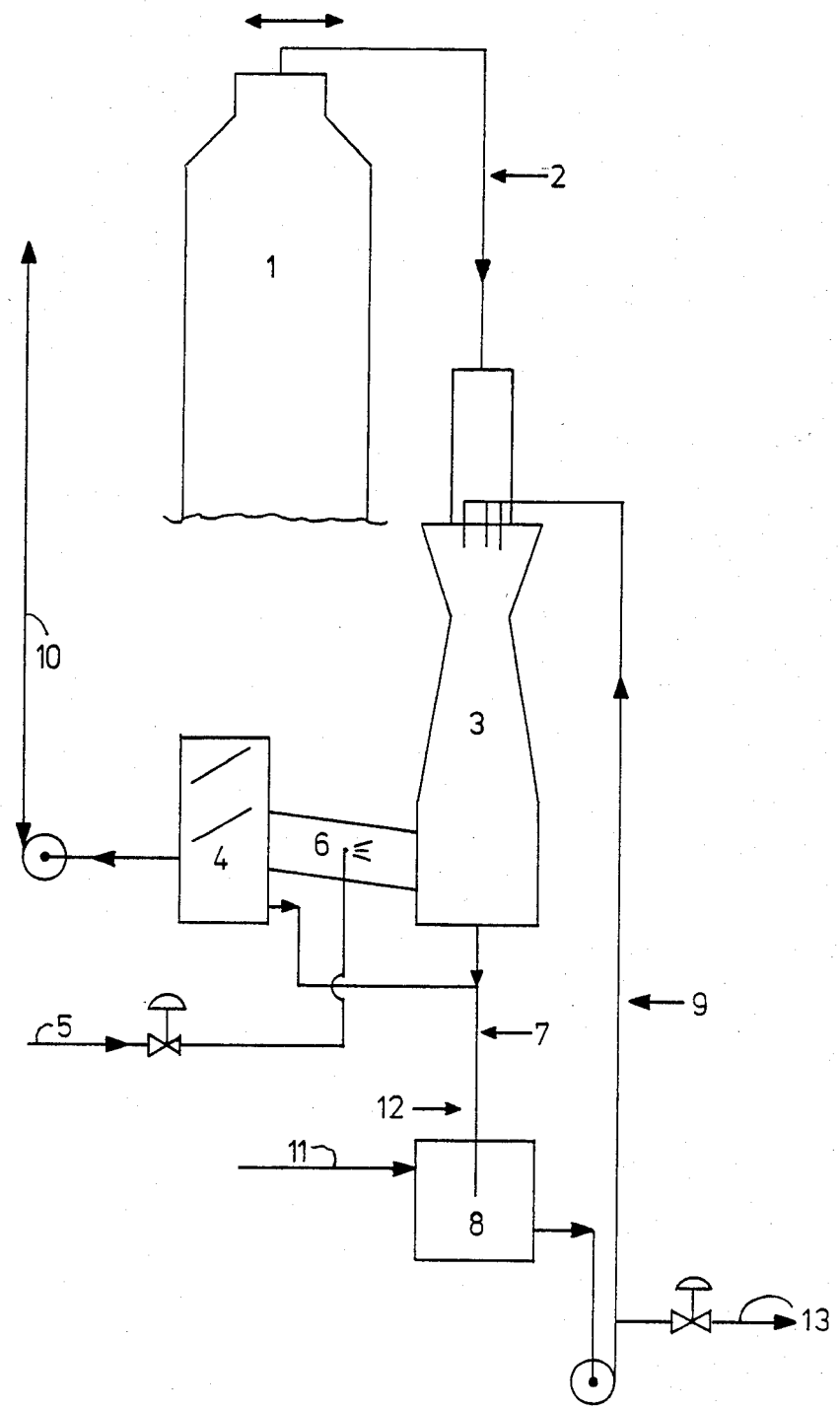
FIG. 1 is a schematic illustation of a prilling tower for urea and a scrubber.

In FIG. 1 is shown a prilling tower 1, from which off-gases are led through pipes 2 to a venturi scrubber 3. Clean water is supplied via pipe 5 to nozzles 6 ahead of a demister 4. The washing solution from the scrubber is conducted through pipe 7 to a circulating tank 8, from which it is pumped back to the venturi scrubber 3 through pipe 9. Cleaned off-gases from the droplet demister 4 are discharged to an exhaust such as a pipe 10 or stack. A urea containing washing solution is continuously removed from the circulation tank 8 and conducted through pipe 13 back to the urea plant. Formaline is supplied through pipe 11 into the circulating tank 8. This supply is controlled by means of an instrument 12 which measures pH in the pipe 7 just before the solution reaches the tank 8.

Figure 2:
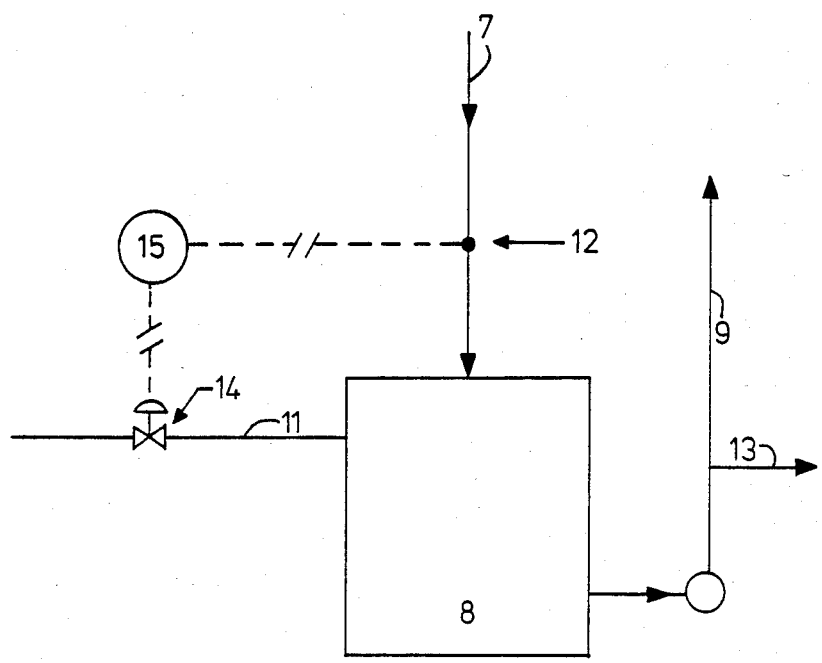
FIG. 2 is a schematic illustration of details of the formaline supply to the scrubber.

The supply of formaldehyde is shown in more detail in FIG. 2. The aqueous formaldehyde solution (formaline) is supplied through pipe 11 to the circulating tank 8. The amount is regulated by a valve 14 which is controlled from the pH-measurements in pipe 7 by means of the instrument 12. The pH is registered by a control unit 15. The signal from this unit is used to control the regulating valve 14. Formaline or formaldehyde in other forms can first be mixed with water in a separate mixing tank to the desired concentration and then supplied through pipe 11. This mixing operation is not shown on the drawing.

EXAMPLE 1

The cleaning unit for off-gases was started by applying a circulated aqueous urea solution. Clean water was supplied to the unit in such amounts that the desired concentration of urea in the aqueous solution was obtained, and part of the solution was continuously purged and returned to the urea plant. At a production of 620 tons of urea/day, measurement of the ammonia emission in the gases leaving the scrubber was 11.4 kg/h. The pH in the washing solution was about 8.7. The washing solution faded and an increasing precipitation of solid particles and accretion in the scrubber occurred.

EXAMPLE 2

The cleaning unit was run as in Example 1, but now formaldehyde was added. Addition of formaldehyde was started after having noticed a definite precipitation, which soon disturbed the performance of the cleaning unit. Shortly afterwards the precipitated particles now dissolved and the solution became completely clear, and after some time even the deposits in the scrubber dissolved. The pH of the washing solution was reduced when formaldehyde was added. Emission of ammonia in the gases leaving the scurbber was recorded and proved to be reduced as a result of the improved washing by a washing solution having a lower pH.

There was now run a series of experiments in which the amount of formaldehyde in the washing solution was varied. When decreasing amounts of formaldehyde were used, it was noticed that first the emission of ammonia increased and the pH in the washing solution also increased. Further reduction of addition of formaldehyde resulted in fading of the washing solution and precipitation of the washing solution and precipitation of solids which dissolved again as soon as more formaldehyde was added. It was found that even small amounts of formaldehyde in the solution had a positive effect on preventing precipitation and accretion in the scrubber. Addition of larger amounts of formaldehyde resulted in reduced ammonia emission. It was found to be advantageous to keep the pH of the washing solution at pH=6–8.5, preferably pH=7, in order to obtain as good results as possible regarding low ammonia emission. It was experienced that an addition of formaline corresponding to about 1 kg $CH_2O$ per ton urea produced gives acceptable results.

Thus it was found advantageous to apply the pH of the washing solution as a parameter for controlling the addition of formaldehyde. This is especially advantageous when it also is desired to obtain optimal removal of ammonia. Other parameters for the addition of formaldehyde can of course be applied. Constant amounts of formaldehyde can be used and also visual surveyance of precipitation which are shown by fading of the washing solution.

At which part of the cleaning unit formaldehyde should be added and in which form, has to be chosen in view of the practical performance of the unit. The determining factor is that the washing solution must contain formaldehyde and in desired amounts so that accretion is avoided and that absorption of ammonia is as good as possible.

The formaldehyde added to the washing solution will later on end up in the urea product. It has been found that the amount of formaldehyde added during the urea production in order to obtain products having a high crushing strength, can be reduced corresponding to the amount of formaldehyde added via the washing unit. It might even be possible to add all the formaldehyde necessary for increasing the crushing strength via the cleaning unit.

The present invention has made it possible to prevent precipitation and plugging of the scrubber and also doubling the removal of ammonia without increasing the addition of additives during the urea production. Further, there has been found a method for dissolving deposits in the scrubber if such deposits have been formed, for instance during stops of supply of formaldehyde to the washing solution.

The method which has been developed gives minimum performance and investment costs and can easily be applied in a standard cleaning unit for washing off-gases from a urea plant. The advantages of known units will be retained at the same time as better performance and better cleaning of the off-gases are retained by using the invention. These advantages are obtained by applying chemicals which do not pollute the product or disturb the production of urea. The cost of chemicals will be as before.

The degree of removal of ammonia from the off-gases was increased from about 30% to about 70%, and in the unit used for the above experiments this means that the emission of ammonia was reduced from about 10 kg/h to below 5 kg/h.

I claim:

1. In a method for cleaning a dust-containing gas mixture from a urea plant, wherein said gas mixture is washed by an aqueous solution, the improvement comprising:
    adding formaldehyde to said aqueous washing solution before bringing said solution into contact with said gas mixture.

2. The method claimed in claim 1, comprising adding said formaldehyde in the form of formaline.

3. The method claimed in claim 2, further comprising measuring the pH of said washing solution, and regulating the addition thereto of said formaline to maintain said pH from 6–8.5.

4. The method claimed in claim 3, comprising continuously adding a controlled amount of said formaline to said washing solution to maintain said pH at about 7.

* * * * *